US008940890B2

(12) United States Patent
Ji et al.

(10) Patent No.: US 8,940,890 B2
(45) Date of Patent: Jan. 27, 2015

(54) PREPARATION METHOD OF 5-[[2(R)-[1(R)-[3,5-BIS(TRIFLUOROMETHYL)PHENYL]ETHOXY]-3(S)-4-FLUOROPHENYL-4-MORPHOLINYL]METHYL]-1,2-DIHYDRO-3H-1,2,4-TRIAZOLE-3-ONE

(75) Inventors: Jianxin Ji, Sichuan (CN); Qiang Zhang, Sichuan (CN); Fengtian Du, Sichuan (CN); Yi Jin, Sichuan (CN); Tao Zhang, Sichuan (CN); Na Guo, Sichuan (CN); Xiaowei Yan, Sichuan (CN); Yongrongn Yang, Sichuan (CN); Bogang Li, Sichuan (CN)

(73) Assignee: Chengdu DI'AO Pharmaceutical Group Co., Ltd., Chengdu, Sichuan (CN)

( * ) Notice: Subject to any disclaimer, the term of this patent is extended or adjusted under 35 U.S.C. 154(b) by 0 days.

(21) Appl. No.: 13/700,007

(22) PCT Filed: May 20, 2011

(86) PCT No.: PCT/CN2011/074372
§ 371 (c)(1),
(2), (4) Date: Nov. 26, 2012

(87) PCT Pub. No.: WO2011/147279
PCT Pub. Date: Dec. 1, 2011

(65) Prior Publication Data
US 2013/0109853 A1 May 2, 2013

(30) Foreign Application Priority Data

May 24, 2010 (CN) .......................... 2010 1 0181849

(51) Int. Cl.
*C07D 265/32* (2006.01)
*C07D 413/06* (2006.01)
(52) U.S. Cl.
CPC ............ *C07D 413/06* (2013.01); *C07D 265/32* (2013.01)
USPC .......................................... 544/132; 544/162
(58) Field of Classification Search
CPC .............................. C07D 265/32; C07D 249/12
See application file for complete search history.

(56) References Cited

U.S. PATENT DOCUMENTS 5,719,147 A  2/1998 Dorn et al.
6,096,742 A  8/2000 Crocker et al.

FOREIGN PATENT DOCUMENTS

| CN | 1646525 | 7/2005 |
| IN | 20080135813 | 1/2010 |
| IN | 2008MU01358 A | * 8/2010 |
| WO | WO2007/039883 | 4/2007 |
| WO | WO2007044829 | 4/2007 |
| WO | WO2009/001203 | 12/2008 |
| WO | WO2009/116081 | 9/2009 |
| WO | WO 2010092591 A2 | * 8/2010 |

OTHER PUBLICATIONS

International Search Report; International Application No. PCT/CN2011/074372; International Filing Date: May 20, 2011; 6 pages. English Translation.
Brands, Karel M.J., "Efficient Synthesis of NK Receptor Antagonist Aprepitant Using a Crystallization-Induced Diastereoselective Transformation"; Journal of the American Chemical Society (2003); 8 pages.
English Abstract of Chinese PCT Publication; International Application No. PCT/CN2011/074372; International Filing Date: May 20, 2011; 1 page.
Cowden, Cameron J., et al.; "A new synthesis of 1,2,4-triazolin-5-ones: application to the convergent synthesis of an NK1 antagonist"; Tetrahedron Letters 41 (2000) 8661-8664.
Chandrashekar R. Elati, et al.; A convergent approach to the synthesis of aprepitant:a potent human NK-1 receptor antagonist. Tetrahedron Letters 48 (2007) 8001-8004.
Finke, Paul E., et al.; Cyclopentane-based human NK1 antagonists. Part 1: Discovery and initial SAR Bioorganic & Medicinal Chemistry Letters 16 (2006) 4497-4503.
Elmore, Charles S. et al., The Syntheses of [$^{14}$C] and [$^{13}$C$_2$, $^{15}$N$_3$] aprepitant; Journal of Labeled Compounds & Radiopharmaceuticals (2004), 10 pages.
English abstract; Chinese Application No. CN1646525; 1 page, (2003).

* cited by examiner

*Primary Examiner* — Nyeemah A Grazier
(74) *Attorney, Agent, or Firm* — Blank Rome LLP

(57) ABSTRACT

Disclosed is a synthesis method of a compound of formula 1,5-[[2(R)-[1(R)-[3,5-bis(trifluoromethyl)phenyl]ethoxyl]-3(S)-4-fluorophenyl-4-morpholinyl]methyl]-1,2-dihydro-3H-1,2,4-triazole-3-one (i.e. aprepitant), which comprises cyclizing a compound of formula 4 in a solvent, wherein R is $C_1$-$C_5$ alkyl. The intermediate for preparing aprepitant is also disclosed. The present method is especially suitable for industrial production of aprepitant.

18 Claims, No Drawings

PREPARATION METHOD OF 5-[[2(R)-[1(R)-[3,5-BIS(TRIFLUOROMETHYL)PHENYL]ETHOXY]-3(S)-4-FLUOROPHENYL-4-MORPHOLINYL]METHYL]-1,2-DIHYDRO-3H-1,2,4-TRIAZOLE-3-ONE

FIELD OF THE INVENTION

The present invention belongs to the field of pharmaceutical technology, particularly relates to a new synthesis method of the compound 5-[[2(R)-[1(R)-[3,5-bis(trifluoromethyl)phenyl]ethoxy]-3(S)-4-fluorophenyl-4-morpholinyl]methyl]-1,2-dihydro-3H-1,2,4-triazole-3-one (Aprepitant).

BACKGROUND OF THE INVENTION

The structure of 5-[[2(R)-[1(R)-[3,5-bis(trifluoromethyl)phenyl]ethoxy]-3(S)-4-fluorophenyl-4-morpholinyl]methyl]-1,2-dihydro-3H-1,2,4-triazole-3-one (i.e., aprepitant) is as follows:

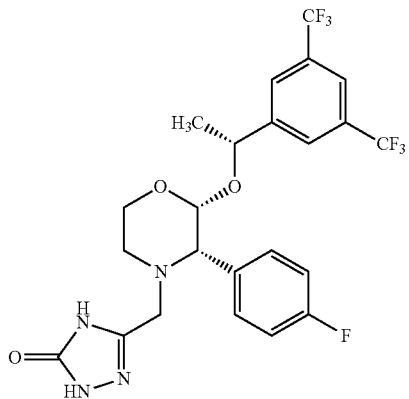 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

Aprepitant is the first substance P/neurokinin 1 (NK1) receptor antagonist developed by Merck & Co., which has selectivity and highly affinity for NK1 receptor, and has no affinity for 5-HT$_3$, dopamine and corticosteroid receptors. Aprepitant was first approved by FDA in March 2003 for marketing in the United States, and was then successively marketed in other countries in the world, which is mainly used for the treatment of nausea and vomiting induced by chemotherapy, as well as for the treatment of nausea and vomiting after surgical operations.

There are three chiral centers in the chemical structure of aprepitant, which can be resolved to be formed by fragment A connected with fragment B.

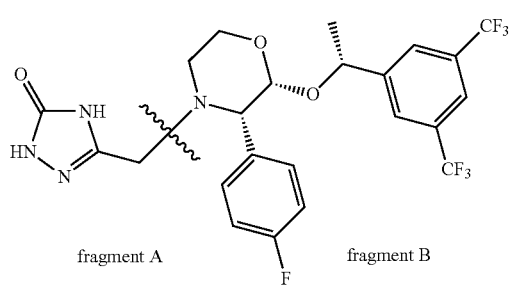

The process for connecting fragments A and B in currently known literatures includes the following two methods.

Method 1

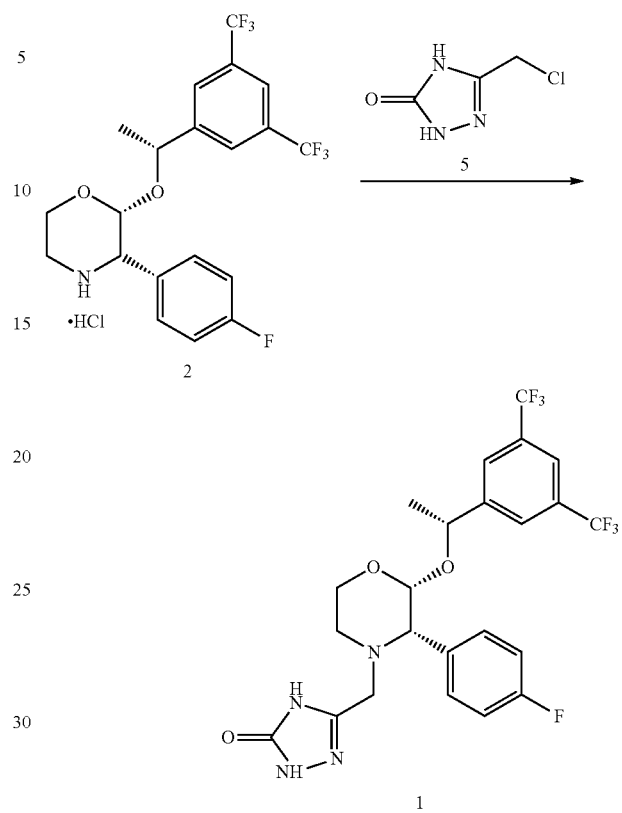

Method 1: WO99/65900; WO01/96315; WO2007/039883 and China patent ZL99807466 report obtaining aprepitant (1) by direct connection of compound 2 and 3-chloromethyl-1,2,4-triazolin-5-one (5). Although there is only one step in this method, the synthesis of the starting material 5 needs four additional steps of chemical reaction, as the operational steps described in literature *Tetrahedron Lett.* 2000, 41, 8661-8664 and China patent ZL99807466, which undoubtedly increases the steps of the operating process of the production, as well as increases the production cost. Furthermore, the reactions are performed in toxic solvents dimethylformamide or acetonitrile, which readily results in organic solvent residue in the final product.

Method 2

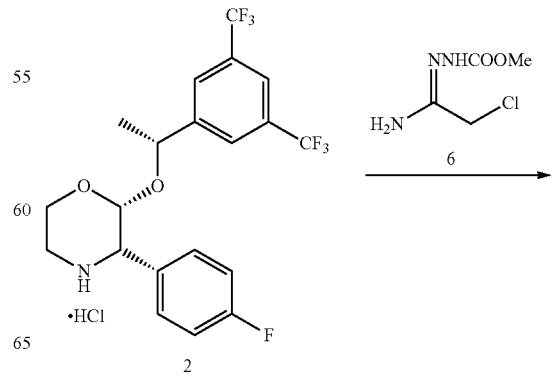

-continued

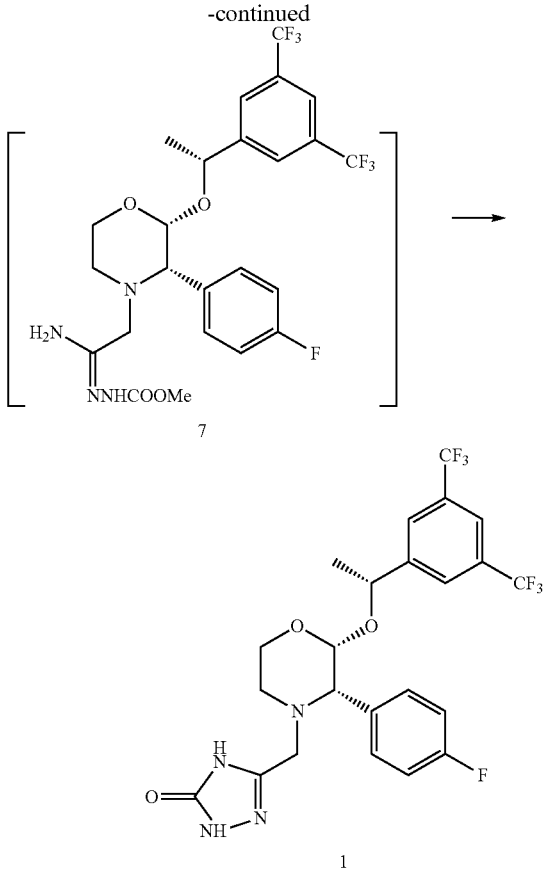

Method 2: *Tetrahedron Lett.* 2007, 48, 8001-8004; *J. Am. Chem. Soc.* 2003, 125, 2129-2135; WO2009/001203; WO2007/044829; WO2007/039883 and China patent ZL03808446 report that first obtaining intermediate product 7 by coupling N-methoxycarbonyl-2-chloroaminoethazone (6) and compound 2, which intermediate product is directly used in the next step cyclization to obtain aprepitant (1), without separation and purification. However, an obvious disadvantage of this method is that a large amount of extremely toxic organic solvents such as toluene, xylene, etc., is used during the cyclization reaction, which is disadvantageous to the environmental protection. Moreover, the cyclization reaction requires a temperature condition of 140-150° C., such a reaction condition requires more energy consumption, and has higher requirements for the temperature-resistant performance of the reaction equipment. Therefore, this method is disadvantagous for the implementation of the industrial production of aprepitant.

Therefore, a new method for preparing aprepitant is still needed to be provided, in order to overcome one or more aspects of problems existed in the prior art mentioned above.

SUMMARY OF THE INVENTION

The present invention discloses a new environment-friendly, low-energy-consuming method for preparing aprepitant. The method is performed by conducting a cyclization reaction in appropriate solvents, so as to minimize the damage of the reaction to the environment. Furthermore, the method of the present invention is also suitable for the industrial production of aprepitant with respect to energy consumption, equipment requirements, etc.

The present invention further relates to a specific intermediate compound for the preparation of aprepitant, and the use thereof in the preparation of aprepitant.

DETAILED DESCRIPTION OF THE INVENTION

Specifically, in the first aspect, the present invention discloses a method for preparing the following compound of Formula 1 (including pharmaceutically acceptable salts thereof):

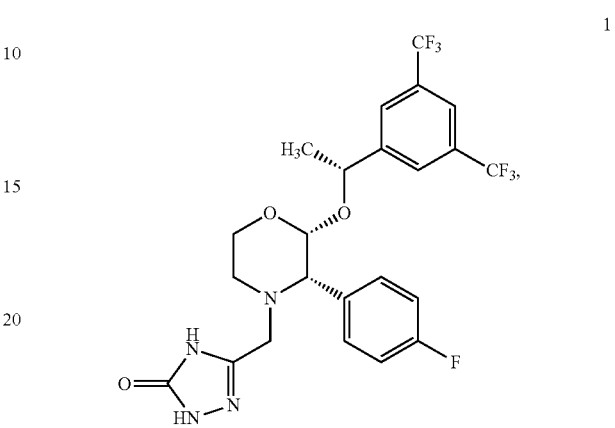

which comprises preparing the compound of Formula 1 by cyclizing the following compound of Formula 4 in a solvent,

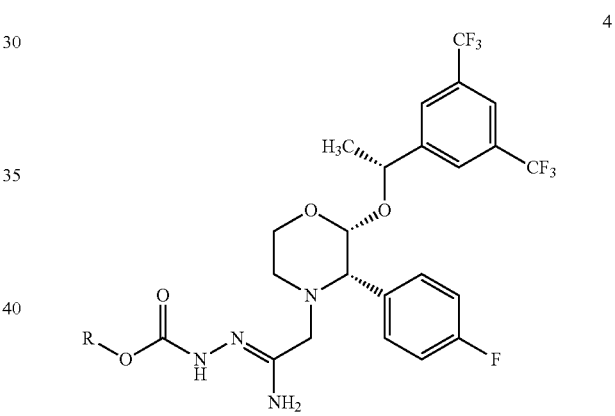

wherein R is selected from $C_1$-$C_5$ alkyl, particularly preferably selected from methyl, ethyl and t-butyl; and the solvent is selected form alcohol, water, alcohol-water mixed solvent, ester, ether and ether-water mixed solvent.

In a preferred embodiment, the alcohol of the present invention is $C_1$-$C_{10}$ fatty alcohol, preferably selected from methanol, ethanol, propanol, n-butanol, t-butanol and propanediol; the ester is an organic acid ester; preferably selected from ethyl acetate, methyl acetate, ethyl formate and t-butyl acetate; the ether is selected from tetrahydrofuran, dioxane and 2-methyl tetrahydrofuran.

In a preferred embodiment, the solvent is alcohol, water or alcohol-water mixed solvent. In another particularly preferred embodiment, the alcohol or the alcohol in the alcohol-water mixed solvent of the present invention is $C_1$-$C_{19}$ fatty alcohol, preferably selected from methanol, ethanol, propanol, n-butanol, t-butanol and propanediol; the ether in the ether-water mixed solvent is selected from tetrahydrofuran, dioxane and 2-methy tetrahydrofuran. In another preferred embodiment of the present invention, the solvent is ethanol-water mixed solvent; in a particularly preferred embodiment, the volume ratio of the ethanol-water mixed solvent is 1:0.1 to 1:100.

In yet another preferred embodiment of the present invention, the solvent is ether-water mixed solvent. In another particularly preferred embodiment the ether-water mixed solvent is tetrahydrofuran-water mixed solvent; wherein in a particularly preferred embodiment, the volume ratio of the ether-water mixed solvent is 1:0.1 to 1:100.

In some preferred embodiments of the present invention, the cyclization reaction is carried out under the action of an inorganic base, wherein the inorganic base can be selected from $KHCO_3$, $K_2CO_3$, $Na_2CO_3$, $NaHCO_3$, KOH, NaOH and $Cs_2CO_3$, preferably selected from KOH or NaOH.

Optionally, the method of the present invention further comprises washing the organic phase containing the compound of Formula 4 using aqueous phase before the cyclyzation, wherein the aqueous phase comprises an aqueous solution of a salt. Preferably, the salt is selected from KCl, $KHCO_3$, $K_2CO_3$, $Na_2CO_3$, $NaHCO_3$, NaCl and a combination thereof.

In a particularly preferred embodiment of the method according to the present invention mentioned above, the compound of Formula 4 is obtained by a reaction between the compound of Formula 2

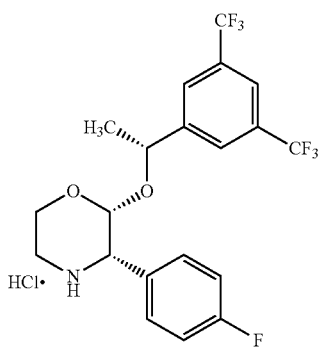

2 and the compound of Formula 3

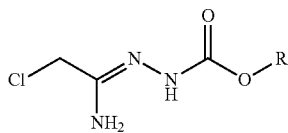

3 in a solvent, wherein R is selected from $C_1$-$C_5$ alkyl; and the solvent is selected from alcohol, water, alcohol-water mixed solvent, ether, ester and ether-water mixed solvent. Compound 2 can be obtained in accordance with the methods described in literatures *J. Am. Chem. Soc.* 2003, 125, 2129-2135 and China patent ZL01810896, and compound 3 can be obtained in accordance with the methods described in WO9410165, WO9321181, *J. Labelled Compd. Radiopharm.* 2004, 47, 837-846, and *Bioorg. Med. Chem. Lett.* 2006, 16, 4447-4503, etc.

In the second aspect, the present invention relates to a compound having the following structure:

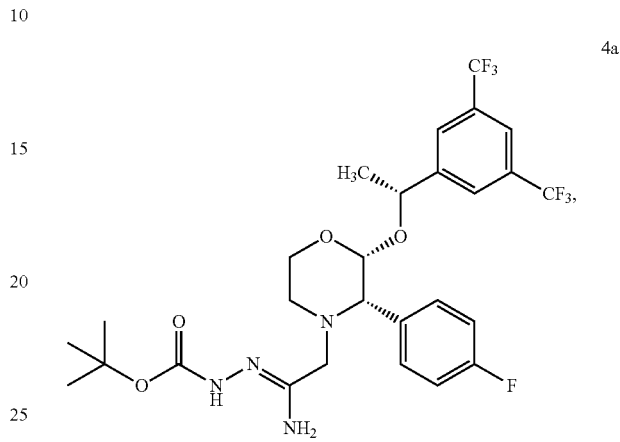

4a

The preparation method and structural characterization data thereof are detailed in Example 1.

The above-mentioned compound of Formula 4a can be used directly in the cyclization reaction of the present invention to prepare the compound of Formula 1. Therefore, in another aspect of the present invention, the present invention relates to the use of the compound of Formula 4a mentioned above as an intermediate compound for the preparation of the compound of Formula 1.

The process route of the present invention described above is a process for the preparation of aprepitant which is green chemistry-based, extremely environmental-friendly, and/or has advantages of low energy consumption, high safety, etc. The synthesis method of the present invention is more suitable for the industrial production of aprepitant compared with methods in the prior art.

The following Examples are provided to further illustrate the present invention and the embodiments thereof. However, it should be appreciated that the specific content in the Examples is only for the purpose of illustration, and should not be construed as limitation to the present invention.

Example 1

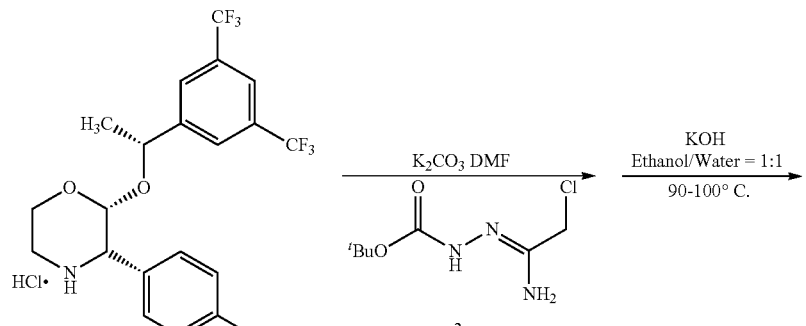

2

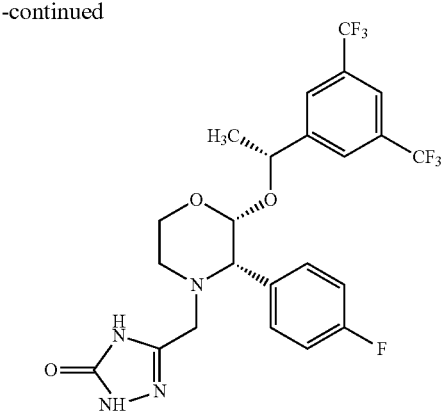

A mixture of starting materials (2R,3S)-2-[(1R)-1-[3,5-bis (trifluoromethyl)phenyl]ethoxy]-3-(4-fluorophenyl)morpholine hydrochloride 2 (2 kg; 4.23 mol) and potassium carbonate (1.75 kg; 12.7 mol) was cooled to about 10° C. in the solvent N,N-dimethyl formamide (DMF). A slurry of amidrazone 3a (962 g; 4.65 mol) dissolved in DMF (4 L) was added. The reaction mixture was stirred at room temperature. The mixture was extracted with ethyl acetate (6 L) and water (8 L) and then phases weere separated after the reaction was completed, the layer of ethyl acetate was washed with saturated aqueous solution of NaCl (8 L×3) and combined, the majority of organic solvent ethyl acetate (about 20 L) was recovered under normal pressure, to obtain intermediate 4a. The intermediate 4a was directly put into the next step of reaction without separation. A water-ethanol mixed solvent and about 400 g potassium hydroxide was added into a reaction bottle, the reaction solution was reacted for about 1 hour at about 90-100° C., the majority of organic solvent ethanol was recovered under normal pressure after the reaction was completed. The reaction solution was cooled to room temperature, and a large amount of solid precipitated. Purifying steps: the above-mentioned solid was filtrated, and dried in vacuum at 40° C. The resultant product was dissolved in methanol (10 L), decolorized by adding appropriate amount of activated carbon, the mixture was heated and refluxed for 1 hour at about 60° C., and filtrated at the same temperature. The filtrate was cooled to room temperature, and a large amount of water was added slowly to the filtrate. The slurry was cooled to about 5° C. Solid was filtrated and dried in vacuum at 40° C., to obtain the product aprepitant (1940 g, 86%).

Spectroscopic date of the intermediate 4a:

$^1$HNMR (600 MHz, CDCl$_3$): δ 7.64 (s, 1H), 7.35 (brs, 2H), 7.16 (s, 2H), 7.03 (t, J=8.4 Hz, 2H), 5.47 (s, 1H), 4.88 (dd, J=12.8, 6.6 Hz, 1H), 4.34 (d, J=2.22 Hz, 1H), 4.23 (t, J=11.6 Hz, 1H), 3.64 (d, J=10.7 Hz, 1H), 3.43 (s, 1H), 3.27 (d, J=14.3 Hz, 1H), 2.95 (d, J=12.1 Hz, 1H), 253-2.44 (m, 2H), 1.45 (s, 9H). $^{13}$CNMR (150 MHz, CDCl$_3$): δ 163.5, 161.8, 154.9, 145.4, 132.4, 132.0, 131.7, 131.5, 131.3, 130.7, 130.6, 126.2, 123.9, 122.1, 121.4, 115.4, 115.2, 95.4, 72.3, 68.8, 59.4, 56.4, 52.4, 28.3, 24.4, MS (EI) m/z: 608.81 (M+1).

Spectroscopic data of aprepitant:

$^1$H NMR (CD$_3$OD, 600 MHz): δ 7.69 (s, 1H), 7.41 (br, s, 2H), 7.22 (s, 2H), 6.95 (t, J=8.7 Hz, 2H), 4.85 (q, J=6.6 Hz, 1H), 4.27 (d, J=2.9 Hz, 1H), 4.19 (dt, J=2.3, 11.6 Hz, 1H) 3.57 (d, J=6.6 Hz, 1H), 3.44 (d, J=14.3 Hz, 1H), 2.78 (m, 1H), 2.40 (dt, J=3.5, 11.8 Hz, 1H), 1.35 (d, J=6.6 Hz, 3H), $^{13}$C NMR (CD$_3$OD, 150 MHz): δ 163.4, 161.8, 157.2, 146.1, 145.5, 132.7, 131.6, 131.4, 131.0, 130.9, 126.4, 124.1, 122.3, 120.8, 114.7, 114.6, 95.7, 72.3, 69.0, 59.0, 52.2, 50.8, 23.2. HR-ESI-MS: 557.1389, (C$_{23}$H$_{21}$F$_7$N$_4$NaO$_3$ cal. 557.1399).

Example 2

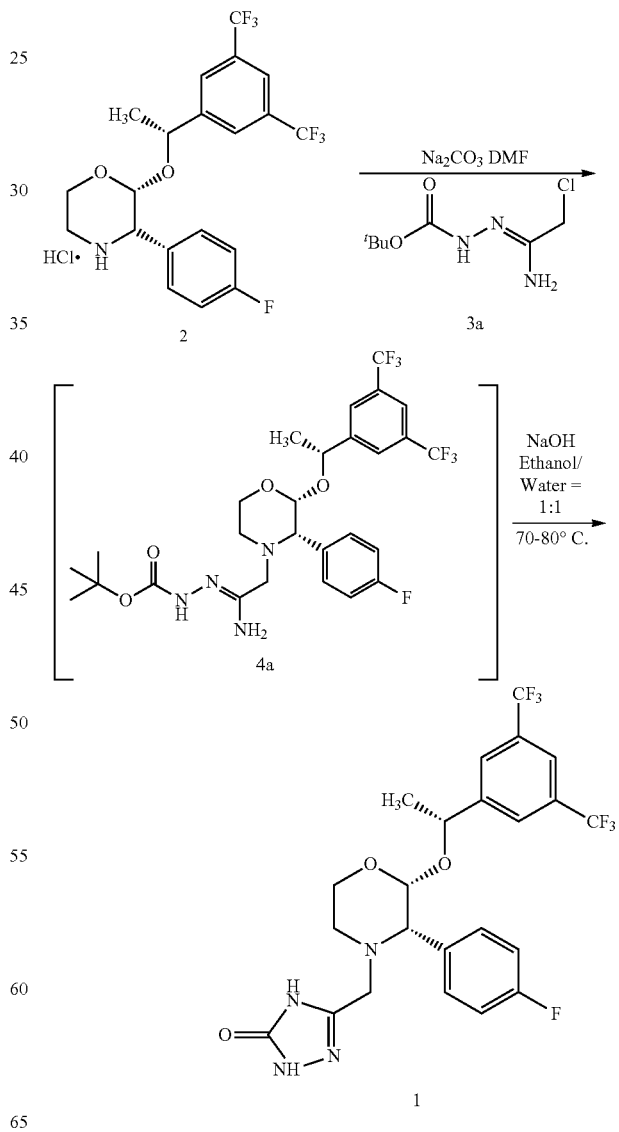

A mixture of starting materials (2R,3S)-2-[(1R)-1-[3,5-bis (trifluoromethyl)phenyl]ethoxy]-3-(4-fluorophenyl)morpholine hydrochloride 2 (5 g; 10.5 mmol) and sodium carbonate (3.5 g; 30 mmol) was cooled to about 10° C. in the solvent DMF. A slurry of amidrazone 3a (2.4 g; 11.6 mol) dissolved in DMF was added. The reaction mixture was stirred at room temperature. The mixture was extracted with ethyl acetate and water and then phases were separated after the reaction was completed. The layer of ethyl acetate was washed with saturated aqueous solution of NaCl and combined. Ethyl acetate was concentrated under reduced pressure to obtain oily substance 4a, which was dissolved in a mixed solution of ethanol and water (1:1). Then 2 g of solid sodium hydroxide was added, and the reaction was performed at 70-80° C. for about 2 hours. After the reaction was completed, the majority of ethanol was removed by concentration under reduced pressure. The solution left was poured into a large amount of ice water, and a large amount of solid precipitated, which was then purified according to the method of Example 1 to obtain aprepitant (4.2 g, yield 76%).

Example 3

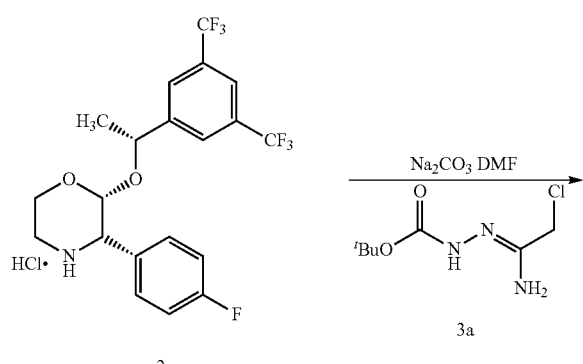

pholine hydrochloride 2 (5 g; 10.5 mmol) and sodium carbonate (3.5 g; 30 mmol) was cooled to about 10° C. in the solvent DMF. A slurry of amidrazone 3a (2.4 g; 11.6 mol) dissolved in DMF was added. The reaction mixture was stirred at room temperature, the mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, to which water was added, and 2 g of solid sodium hydroxide was added. The resultant suspension was reacted at 100° C. for about 5 hours. The above reaction mixture was poured into a large amount of ice water. Solid precipitated, which was then purified according to the method of Example 1 to obtain aprepitant (1.68 g, yield 30%).

Example 4

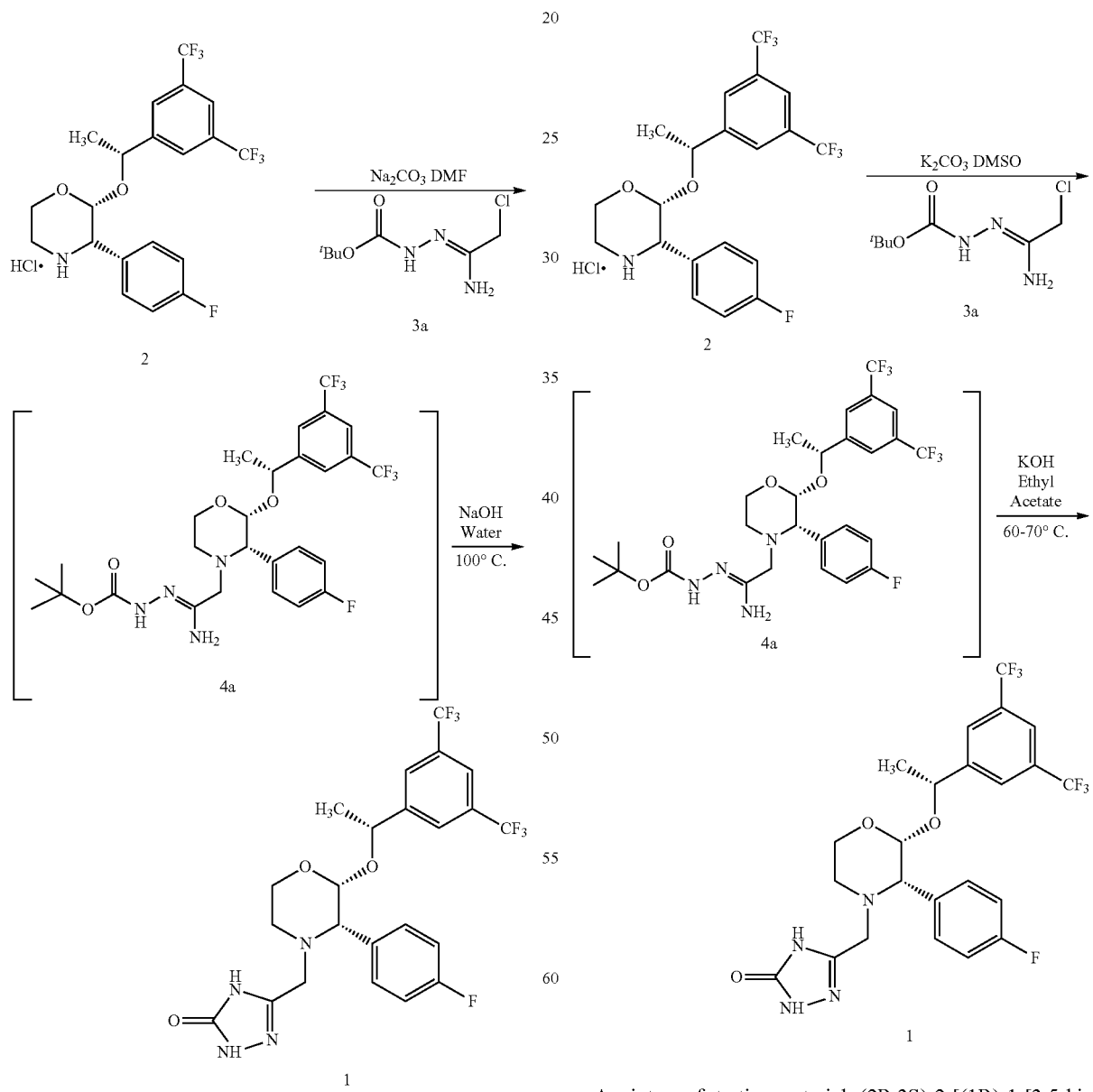

A mixture of starting materials (2R,3S)-2-[(1R)-1-[3,5-bis(trifluoromethyl)phenyl]ethoxy]-3-(4-fluorophenyl)morpholine hydrochloride 2 (5 g, 10.5 mmol) and potassium A mixture of starting materials (2R,3S)-2-[(1R)-1-[3,5-bis(trifluoromethyl)phenyl]ethoxy]-3-(4-fluorophenyl)morcarbonate (2.7 g; 20 mmol) was cooled to about 10° C. in the solvent dimethyl sulfoxide (DMSO). A slurry of amidrazone 3a (2.4 g; 11.6 mol) dissolved in DMSO was added. The reaction mixture was stirred at room temperature. The mixute was extracted with ethyl acetate (6 L) and water (8 L) and phases were separated after the reaction was completed. The layer of ethyl acetate was washed with saturated aqueous solution of KCl and combined. Ethyl acetate was concentrated under reduced pressure to a small volume, and 2 g of solid potassium hydroxide was added, and the reaction was performed at 60-70° C. for about 3 hours. The majority of ethyl acetate was removed by concentrating under reduced pressure. The solution left was poured into a large amount of ice water, and a large amount of solid precipitated, which was then purified according to the method of Example 1 to obtain aprepitant (2.8 g, yield 50%).

Example 5 pholine hydrochloride 2 (5 g; 10.5 mmol) and potassium carbonate (2.7 g; 20 mmol) was cooled to about 10° C. in the solvent DMF, A slurry of amidrazone 3a (2.4 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, which was dissolved in a mixed solution of tetrahydrofuran and water (1:1), and 2 g of solid potassium hydroxide was added. The reaction was performed at 90-100° C. for about 2 hours. The majority of tetrahydrofuran was removed by concentrating under reduced pressure after the reaction was completed. The solution left was poured into a large amount of ice water, and a large amount of solid precipitated, which was then purified according to the method of Example 1 to obtain aprepitant (4.37 g, yield 78%).

Example 6

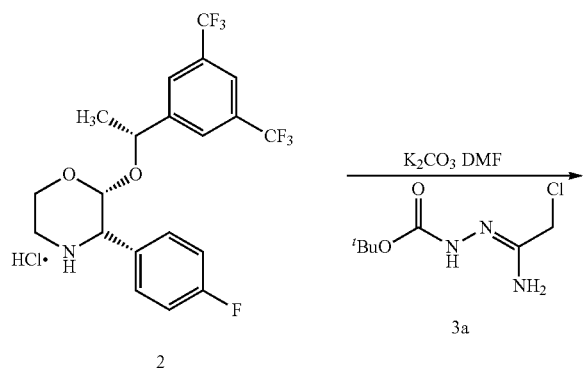

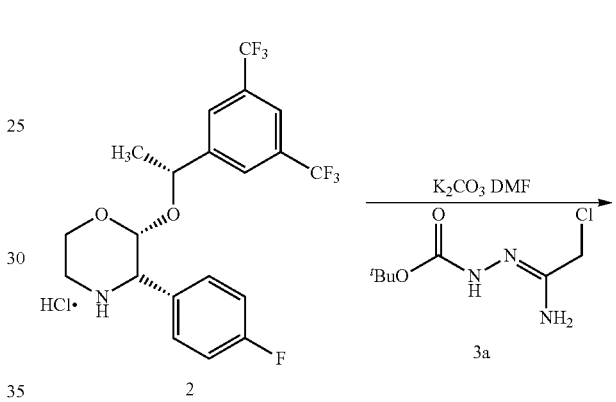

A mixture of starting materials (2R,3S)-2-[(1R)-1-[3,5-bis(trifluoromethyl)phenyl]ethoxy]-3-(4-fluorophenyl)mor- A mixture of starting materials (2R,3S)-2-[(1R)-1-[3,5-bis(trifluoromethyl)phenyl]ethoxy]-3-(4-fluorophenyl)morpholine hydrochloride 2 (5 g; 10.5 mmol) and potassium carbonate (2.7 g; 20 mmol) was cooled to about 10° C. in the solvent DMF. A slurry of amidrazone 3a (2.4 g; 11.6 mol) dissolved, in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, which was dissolved in a solution of ethanol, and 2 g of solid potassium hydroxide was added. The reaction was performed at 90° C. for about 2 hours. The majority of ethanol was removed by concentrating under reduced pressure after the reaction was completed. The solution left was poured into a large amount of ice water, and a large amount of solid precipitated, which was then purified according to the method of Example 1 to obtain aprepitant (3.92 g, yield 70%), pholine hydrochloride 2 (5 g; 10.5 mmol) and potassium carbonate (2.7 g; 20 mmol) was cooled to about 10° C., in the solvent DMF. A slurry of amidrazone 3b (2.07 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oil substance 4b, which was dissolved in a mixed solution of ethanol and water (1:1), and 2 g of solid potassium hydroxide was added. The reaction was performed at 90-100° C. for about 2 hours. The majority of ethanol was removed by concentrating under reduced pressure. The solution left was poured into a large amount of ice water, and a large amount of solid precipitated, which was then purified according to the method of Example 1 to obtain aprepitant (2.92 g, yield 52%).

Example 7

Example 8

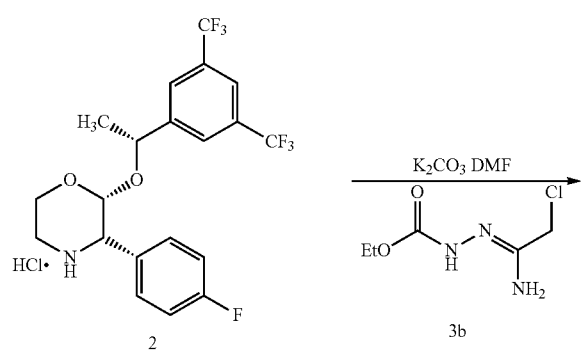

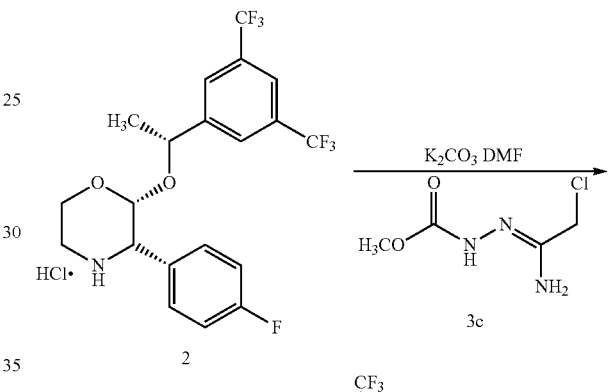

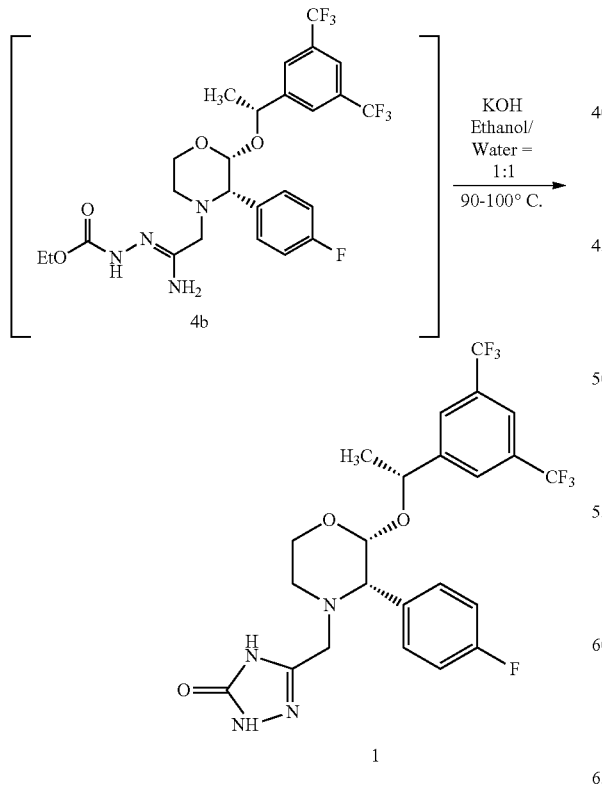

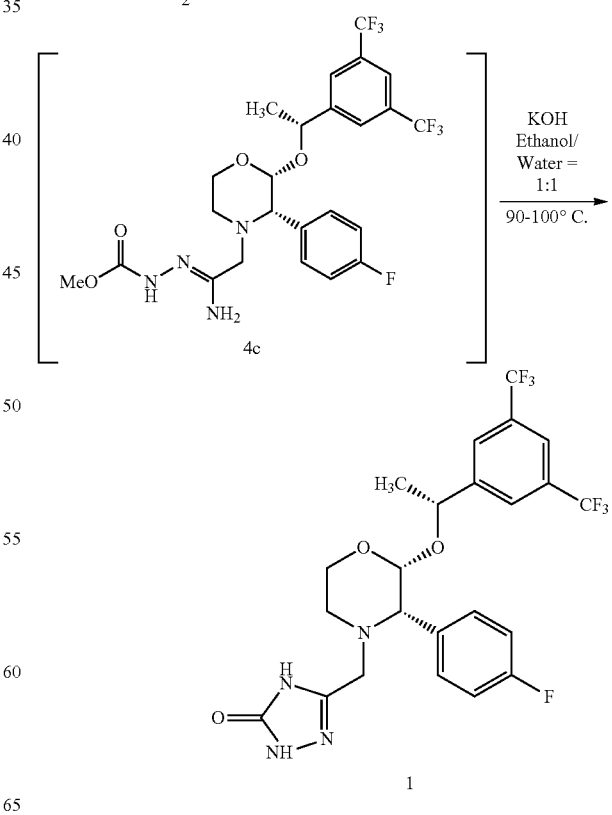

A mixture of starting materials (2R,3S)-2-[(1R)-1-[3,5-bis (trifluoromethyl)phenyl]ethoxy]-3-(4-fluorophenyl)mor- A mixture of starting materials (2R,3S)-2-[(1R)-1-[3,5-bis (trifluoromethyl)phenyl]ethoxy]-3-(4-fluorophenyl)morpholine hydrochloride 2 (5 g; 10.5 mmol) and potassium carbonate (2.7 g; 20 mmol) was cooled to about 10° C. in tha solvent DMF. A slurry of amidrazone 3c (1.91 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4c, which was dissolved in a mixed solution of ethanol and water (1:1) and 2 g of solid potassium hydroxide was added. The reaction was performed at 90-100° C. for about 2 hours. The majority of ethanol was removed by concentrating under reduced pressure. The solution left was poured into a large amount of ice water, and a large amount of solid precipitated, which was then purified according to the method of Example 1 to obtain aprepitant (336 g, yield 60%).

Example 9

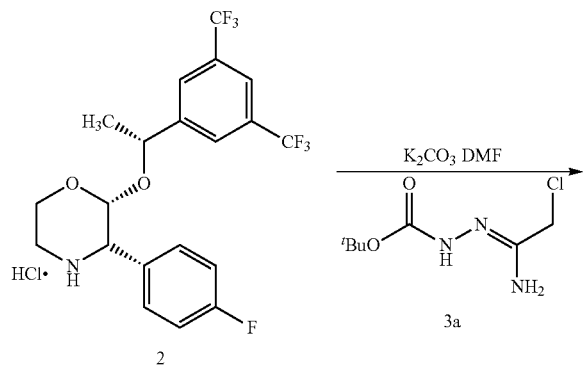

pholine hydrochloride 2 (5 g; 10.5 mmol) and potassium carbonate (2.7 g; 20 mmol) was cooled to about 10° C. in the solvent DMF. A slurry of amidrazone 3a (2.4 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, which was dissolved in a solution of tetrahydrofuran, and 2 g of solid potassium hydroxide was added. The reaction was performed at 60-70° C. for about 12 hours. The majority of tetrahydrofuran was removed by concentrating under reduced pressure. The solution left was poured into a large amount of ice water, and solid precipitated, which was then purified according to the method of Example 1 to obtain aprepitant (1.12 g, yield 20%).

Example 10

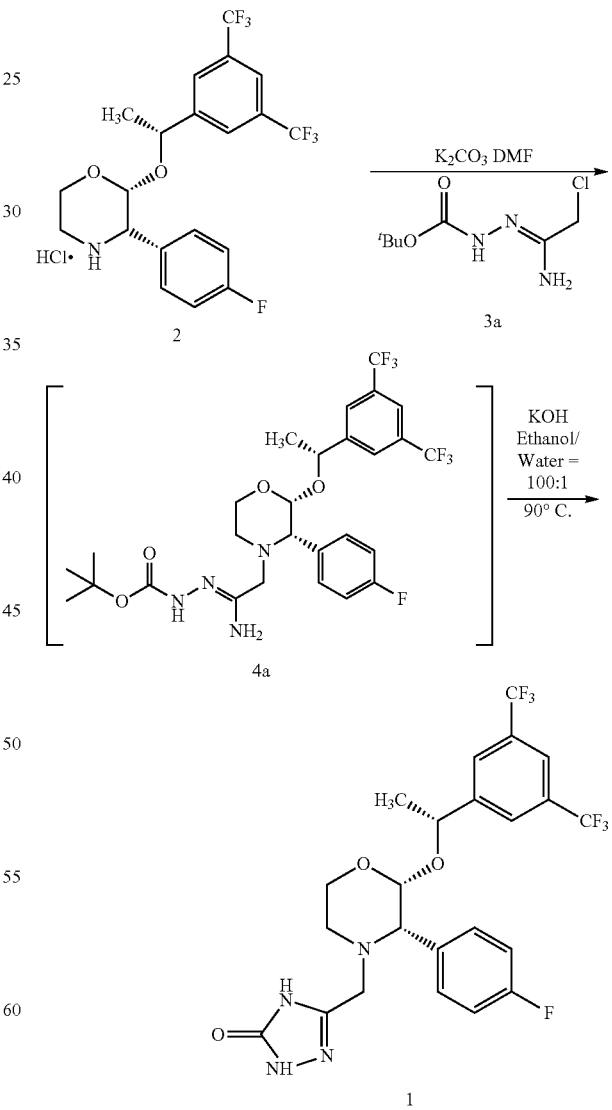

A mixture of starting materials (2R,3S)-2-[(1R)-1-[3,5-bis(trifluoromethyl)phenyl]ethoxy]-3-(4-fluorophenyl)mor- A mixture of starting materials (2R,3S)-2-[(1R)-1-[3,5-bis(trifluoromethyl)phenyl]ethoxy]-3-(4-fluorophenyl)morpholine hydrochloride 2 (5 g; 10.5 mmol) and potassium carbonate (2.7 g; 20 mmol) was cooled to about 10° C. in the solvent DMF. A slurry of amidrazone 3a (2.4 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, which was dissolved in 100 mL solution of ethanol:water=10:1, and 2 g of solid potassium hydroxide was added. The reaction was performed at 90° C. for about 2 hours. The majority of ethanol was removed by concentrating under reduced pressure after the reaction was completed. The solution left was poured into a large amount of ice water, and solid precipitated, which was then purified according to the method of Example 1 to obtain aprepitant (3.2 g, yield 58%).

pholine hydrochloride 2 (5 g; 10.5 mmol) and potassium carbonate (2.7 g; 20 mmol) was cooled to about 10° C. in the solvent DMF. A slurry of amidrazone 3a (2.4 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, which was dissolved in 100 mL solution of water:ethanol=100:1, and 2 g of solid potassium hydroxide was added. The reaction was performed at 100° C. for about 2 hours. After the reaction was completed, the reaction solution was poured into a large amount of ice water, and solid precipitated, which was then purified according to the method of Example 1 to obtain aprepitant (1.8 g, yield 32%).

Example 11

Example 12

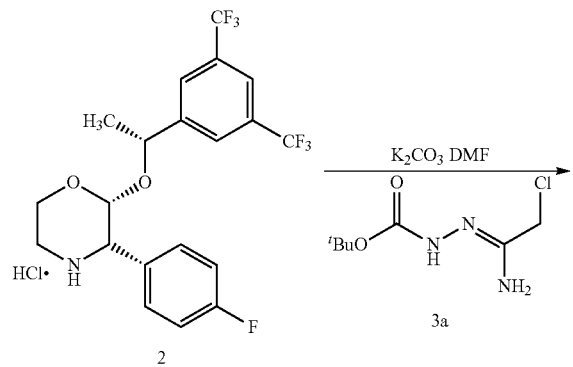

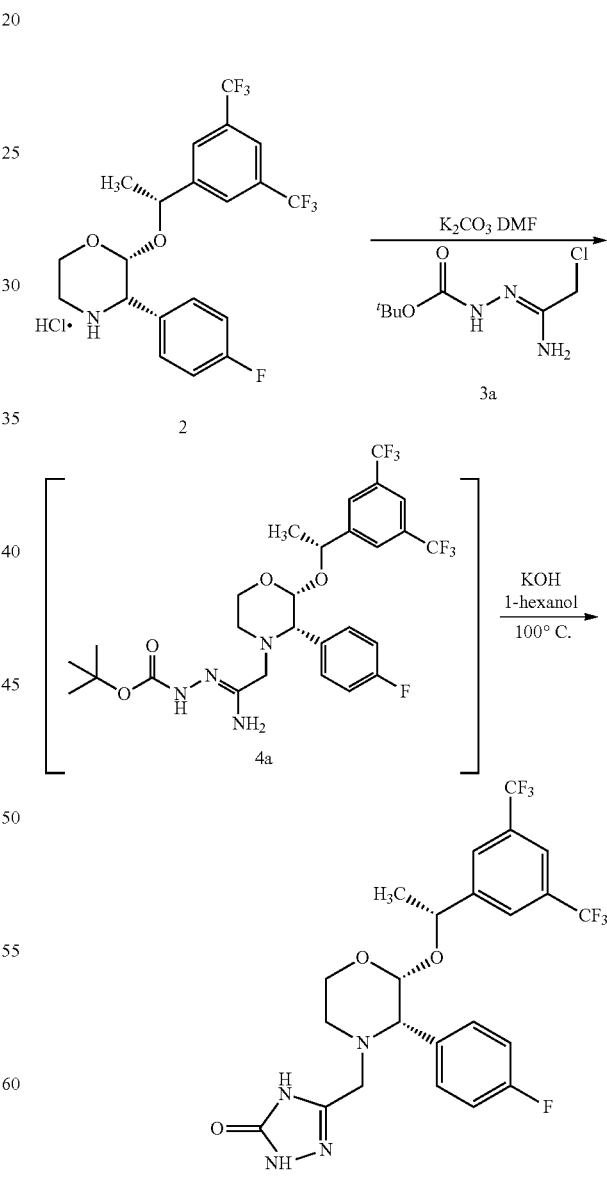

A mixture of starting materials (2R,3S)-2-[(1R)-1-[3,5-bis(trifluoromethyl)phenyl]ethoxy]-3-(4-fluorophenyl)mor- A mixture of starting materials (2R,3S)-2-[(1R)-1-[3,5-bis(trifluoromethyl)phenyl]ethoxy]-3-(4-fluorophenyl)morpholine hydrochloride 2 (5 g; 10.5 mmol) and potassium carbonate (2.7 g; 20 mmol) was cooled to about 10° C. in the solvent DMF. A slurry of amidrazone 3a (2.4 g; 11.6 mol) dissolved in DMF was added. The reaction mixture was stirred at room temperature. The mixture was extracted with ethyl acetate and water and phases were separated after the reaction was completed. The layer of ethyl acetate was washed with saturated aqueous solution of NaCl and combined. Ethyl acetate was concentrated under reduced pressure to obtain oily substance 4a, which was dissolved in a solution of 1-hexanol, and 2 g of solid potassium hydroxide was added. The reaction was performed at 100° C. for about 3 hours. The reaction solution was poured into a large amount of ice water, and solid precipitated, which was then purified according to the method of Example 1 to obtain aprepitant (1.23 g, yield 22%).

Example 13

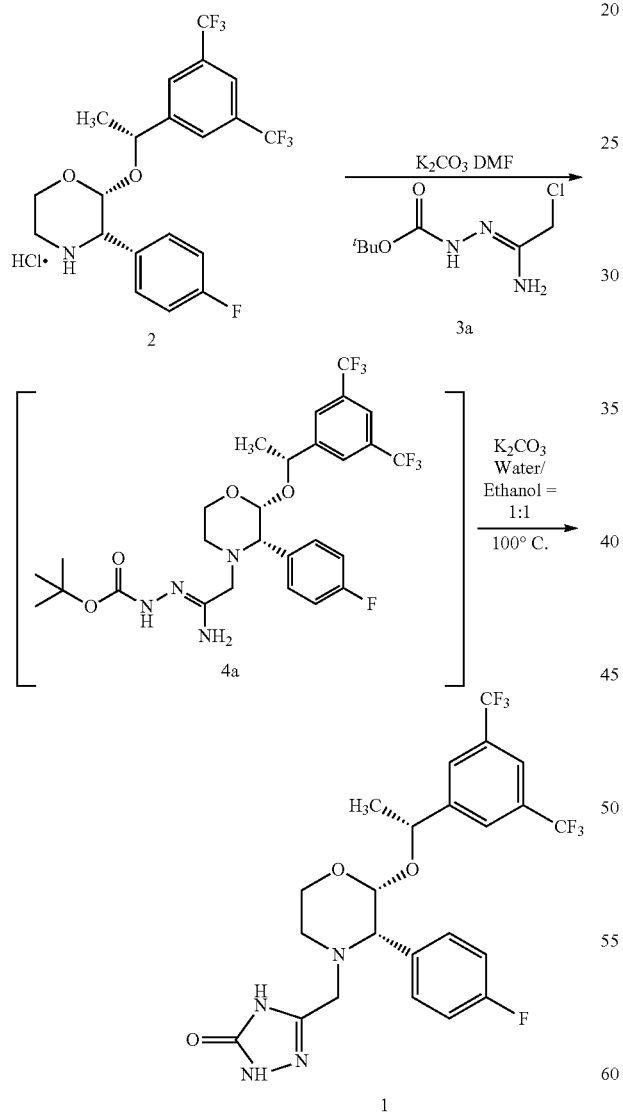

A mixture of starting materials (2R,3S)-2-[(1R)-1-[3,5-bis (trifluoromethyl)phenyl]ethoxy]-3-(4-fluorophenyl)morpholine hydrochloride 2 (5 g; 10.5 mmol) and potassium carbonate (2.7 g; 20 mmol) was cooled to about 10° C. in the solvent DMF. A slurry of amidrazone 3a (2.4 g; 11.6 mol) dissolved in DMF was added. The reaction mixture was stirred at room temperature. The mixture was extracted with ethyl acetate and water and phases weere separated after the reaction was completed. The layer of ethyl acetate was washed with saturated aqueous solution of NaCl and combined. Ethyl acetate was concentrated under reduced pressure to obain oily substance 4a which was dissolved in a solution of water:ethanol=1:1, and 2 g of solid potassium hydroxide was added. The reaction was performed at 100° C. for about 12 hours. After the reaction was completed, the reaction solution was poured into a large amount of ice water, and solid precipitated, which was then purified according to the method of Example 1 to obtain aprepitant (670 mg, yield 12%).

Although various aspects and different embodiments of the present invention have been described in detail by the above-mentioned specific embodiments and examples, it will be appreciated for a person skilled in the art that, based on the above-mentioned teachings, the method and reaction conditions of the present invention can be changed and modified according to specific requirements and actual situations, and all these changes and modifications are considered to fall within the scope of the present invention, i.e., the scope defined by the claims.

The invention claimed is:
1. A method for preparing the following compound of Formula 1:

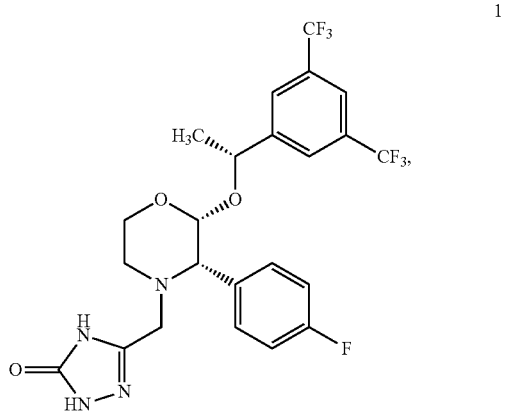 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

which comprises preparing the compound of Formula 1 by cyclizing the following compound of Formula 4 in a solvent:

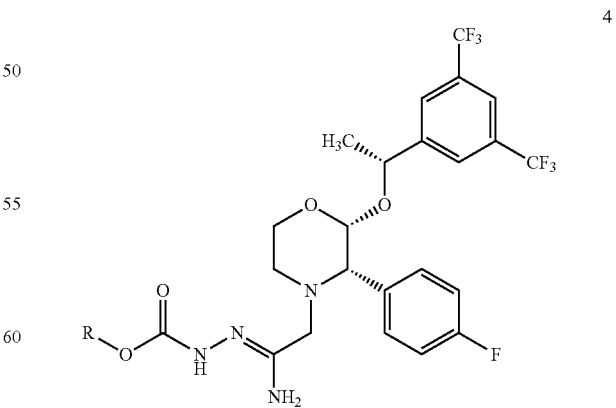

wherein R is t-butyl; and
the solvent is selected from the group consisting of alcohol, water, alcohol-water mixed solvent, ether, ester and ether-water mixed solvent.

2. The method according to claim 1, wherein the alcohol is a $C_1$-$C_{10}$ fatty alcohol; the ester is an organic acid ester; and the ether is selected from the group consisting of tetrahydrofuran, dioxane and 3-methyl tetrahydrofuran.

3. The method according to claim 1, wherein the solvent is alcohol, water or alcohol-water mixed solvent.

4. The method according to claim 1, wherein the solvent is ethanol-water mixed solvent.

5. The method according to claim 4, wherein a volume ratio of ethanol and water is 1:0.1 to 1:100.

6. The method according to claim 1, wherein the solvent is the ether-water mixed solvent.

7. The method according to claim 1, wherein the cyclization reaction is performed under the action of an inorganic base.

8. The method according to claim 1, wherein the temperature of the cyclization reaction is 60 to 100° C.

9. The method according to claim 1, wherein the compound of Formula 4 is obtained by a reaction between a compound of Formula 2

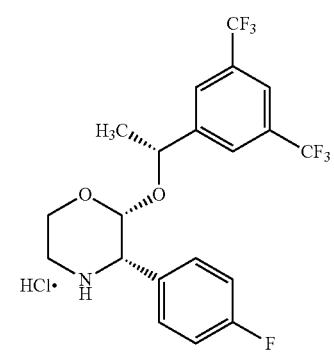

and a compound of Formula 3

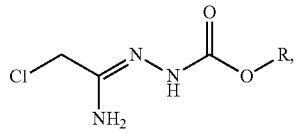

wherein R is t-butyl.

10. The method according to claim 7, wherein the inorganic base is selected from the group consisting of $KHCO_3$, $K_2CO_3$, $Na_2CO_3$, $NaHCO_3$, KOH, NaOH and $Cs_2CO_3$.

11. The method according to claim 7, wherein the inorganic base is KOH or NaOH.

12. The method according to claim 8, further comprising washing the organic phase containing the compound of Formula 4 with an aqueous phase before cyclization, wherein the aqueous phase comprises an aqueous solution of a salt.

13. The method according to claim 12, wherein the salt is selected from the group consisting of KCl, $KHCO_3$, $K_2CO_3$, $Na_2CO_3$, $NaHCO_3$, NaCl and a combination thereof.

14. A compound having the following structure:

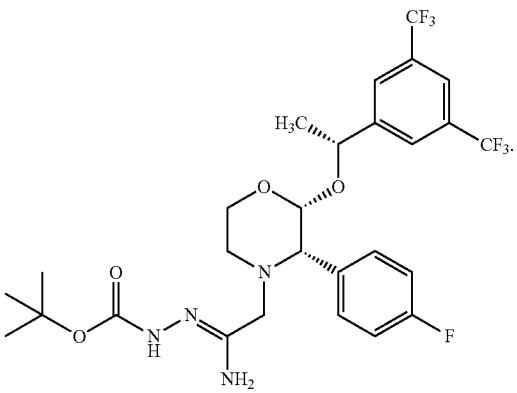 [SMILES: C[C@@H](O[C@H]1OCCN(C/C(N)=N/NC(=O)OC(C)(C)C)[C@H]1c1ccc(F)cc1)c1cc(C(F)(F)F)cc(C(F)(F)F)c1]

15. A method for preparing the compound of Formula 1, comprising using the compound according to claim 14 as an intermediate

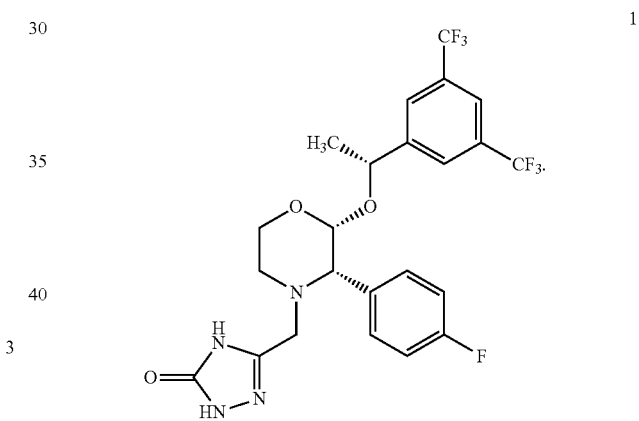

16. The method according to claim 2, wherein the alcohol is selected from the group consisting of methanol, ethanol, propanol, n-butanol, t-butanol and propanediol.

17. The method according to claim 2, wherein the ester is selected from the group consisting of ethyl acetate, methyl acetate, ethyl formate and t-butyl acetate.

18. The method according to claim 6, wherein the ether-water mixed solvent is a tetrahydrofuran-water mixed solvent with a volume ratio of 1:0.1 to 1:100.

* * * * *